United States Patent [19]

Chan et al.

[11] 4,045,475

[45] Aug. 30, 1977

[54] OPTICALLY ACTIVE ALCOHOLS AND LOWER ESTERS THEREOF

[75] Inventors: Ka-Kong Chan, Stanhope; Gabriel Saucy, Essex Fells, both of N.J.

[73] Assignee: Hoffmann-La Roche Inc., Nutley, N.J.

[21] Appl. No.: 723,401

[22] Filed: Sept. 15, 1976

Related U.S. Application Data

[62] Division of Ser. No. 544,153, Jan. 27, 1975, Pat. No. 4,000,169.

[51] Int. Cl.$^2$ .................. C07C 69/145; C07C 69/02; C07C 33/02
[52] U.S. Cl. .................. 260/488 H; 252/522; 260/448.8 R; 260/471 R; 260/475 R; 260/476 R; 260/484 R; 260/485 R; 260/486 AC; 260/563 R; 260/614 R; 260/632 R; 260/632 Y; 260/642 E
[58] Field of Search ............... 260/632 R; 260/488 H

[56] References Cited

U.S. PATENT DOCUMENTS

| 3,121,752 | 2/1964 | Vries | 260/632 R |
| 3,631,179 | 12/1971 | Urry | 260/632 R |
| 3,697,543 | 10/1972 | Pfiffner et al. | 260/488 H |
| 3,859,366 | 1/1975 | Schleppnik | 260/632 R |

FOREIGN PATENT DOCUMENTS

| 777,515 | 6/1957 | United Kingdom | 260/632 R |

OTHER PUBLICATIONS

Braude et al., "J. Chem. Soc.," (1952), pp. 1425 to 1429.

*Primary Examiner*—Joseph E. Evans
*Attorney, Agent, or Firm*—Samuel L. Welt; Bernard S. Leon; William H. Epstein

[57] ABSTRACT

Asymmetric synthesis of optically active 3,7,11-trimethyl-dodecan-1-ol, an intermediate for producing optically active vitamin E, from isovaleraldehyde or prenal including intermediates in this synthesis.

6 Claims, No Drawings

OPTICALLY ACTIVE ALCOHOLS AND LOWER ESTERS THEREOF

CROSS REFERENCE TO RELATED APPLICATIONS

This application is related to U.S. patent application Ser. No. 417,465, filed Nov. 19, 1973, now U.S. Pat. 3,947,473, which is a division of application Ser. No. 544,153 filed Jan. 27, 1975, now U.S. Pat. No. 4,000,169. Scott, Parrish and Saucy, which is incorporated herein by reference.

BACKGROUND OF THE INVENTION

In the past, optically active α-tocopherol and derivatives thereof which are the 2R,4'R,8'R isomers of compounds of the formula:

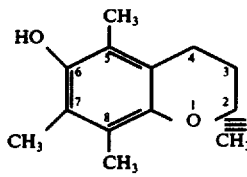

have been prepared through isolation from natural sources such as vegetable oil. This procedure suffers from many drawbacks due to the fact that the tocopherol content of these oils is very small. Therefore, a great amount of oil must be processed in order to isolate a small amount of natural tocopherol. Additionally, the process whereby various tocopherols are isolated from vegetable oil is extremely cumbersome.

In U.S. patent application Ser. No. 417,465, filed Nov. 19, 1973, Scott et al., natural α-tocopherol has been synthesized by reacting via a Wittig reaction a compound of the formula:

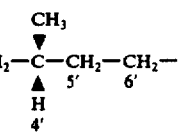

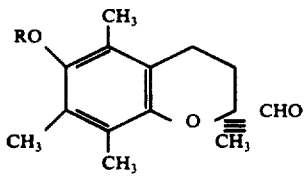

wherein R taken together with its attached oxygen atom forms an ether or ester protecting group removable by hydrogenation or hydrolysis.

(Please note the compound of formula XXVII-A in U.S. application Ser. No. 417,465, filed Nov. 19, 1973) with a dodecanol of the formula:

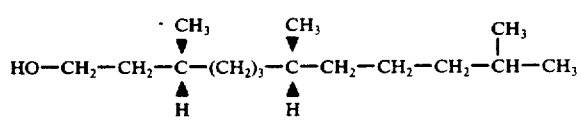

(Please note compound XLVIII-B in U.S. application Ser. No. 417,465). A disadvantage of this process is that the dodecanol of formula III has been difficult to synthesize asymmetrically. In the past, this dodecanol has been produced through degradation of naturally occurring materials such as phytol.

SUMMARY OF THE INVENTION

In accordance with this invention, there is provided a procedure for asymmetrically synthesizing the optically active compound of formula III from isovalderaldehyde or prenal without the need for separating and discarding any unwanted optical isomer. Therefore, in accordance with the process of this invention, the total quantity of isovaleraldehyde or prenal utilized as a starting material is converted to the optically active isomer of formula III and finally to natural α-tocopherol.

The new asymmetric synthesis is achieved in accordance with this invention by the discovery that when a compound of the formula:

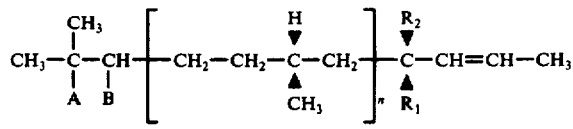

wherein A and B individually are hydrogen or taken together to form a carbon to carbon bond; one of $R_1$ and $R_2$ is hydroxy and the other is hydrogen; n is an integer of from 0 to 1 with the proviso that when $R_1$ is hydrogen, the 2-3 double bond has a trans configuration and when $R_1$ is hydroxy the 2-3 double bond has a cis configuration;

is subjected to Claisen rearrangement, an optically active compound of the formula:

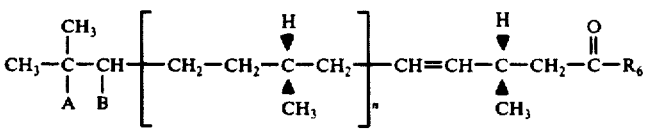

wherein $R_6$ is lower alkoxy, hydrogen,

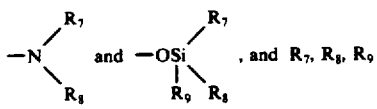

are lower alkyl; and A and B are as above;
is formed which can be directly converted into the optically active compound of formula III.

In accordance with this invention, the compound of formula IV can be either a compound of the formula:

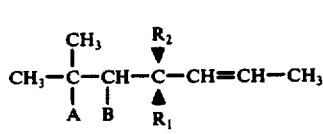

IV-A wherein A and B are as above; $R_1$ and $R_2$ are as above with the proviso that when $R_1$ is hydrogen, the 2-3 double bond has a trans configuration and that when $R_1$ is hydroxy, the 2-3 double bond has a cis configuration;
or a compound of the formula:

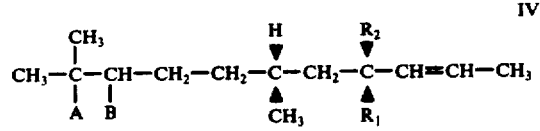

IV-B wherein $R_1$ and $R_2$, A and B are as above and with the proviso that when $R_1$ is hydrogen, the 2-3 double bond has a trans configuration and that when $R_1$ is hydroxy, the 2-3 double bond has a cis configuration.

The compound of formula IV-A when subjected to Claisen rearrangement, produces a compound of the formula:

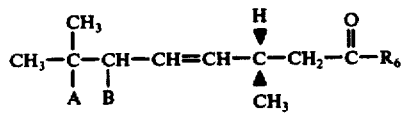

V-A wherein A, B and $R_6$ are as above.

The compound of formula IV-B when subjected to Claisen rearrangement, produces a compound of the formula:

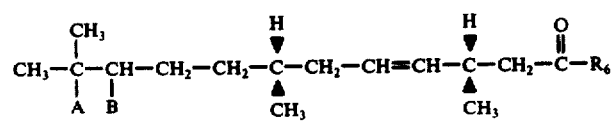

wherein $R_6$, A and B are as above.

DETAILED DESCRIPTION OF THE INVENTION

The numbering of the chain in formula I, III, and V above, is shown for the purpose of convenience.

As used throughout the application, the term "lower alkyl" comprehends both straight and branched chain saturated hydrocarbon groups containing from 1 to 7 carbon atoms such as methyl, ethyl, propyl, isopropyl, etc. As used throughout this application, the term "halogen" includes all four halogens, such as bromine, chlorine, fluorine and iodine. The term "alkali metal" includes sodium, potassium, lithium, etc.

When the term "cis" is utilized in this application, it designates that the two largest substituents attached across the double bond are on the same side of the double bond. The term "trans" as utilized in this application, designates that the largest substituents attached across the double bond are on opposite sides of the double bond.

In the pictorial representation of the compounds given throughout this application, a (▼) tapered line indicates a subsituent which is pointed out of the plane of the paper towards the reader.

The term "lower alkoxy" as used throughout the specification denotes lower alkoxy groups containing from 1 to 7 carbon atoms such as methoxy, ethoxy, propoxy, isopropoxy, etc. The term "lower alkanoyl" as used throughout the specification denotes lower alkanoyl groups containing from 2 to 6 carbon atoms such as acetyl or propionyl.

In accordance with this invention, isovaleraldehyde or prenal is converted to the compound of formula V-A via the following intermediates:

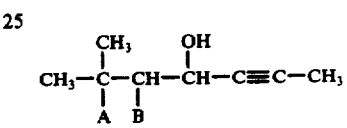

VII

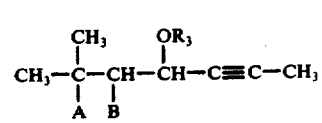

VIII

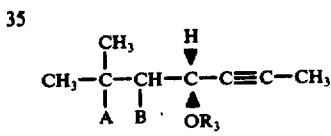

VIII-A

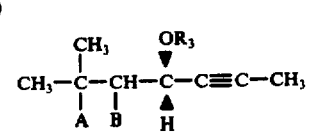

VIII-B

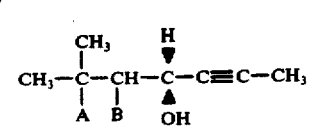

VII-A

V-B

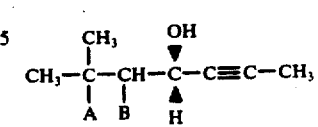

VII-B

-continued $$\text{CH}_3-\underset{\underset{A}{|}}{\overset{\overset{CH_3}{|}}{C}}-\underset{\underset{B}{|}}{CH}-\overset{\overset{H}{\blacktriangledown}}{\underset{\underset{OH}{|}}{\underset{\blacktriangle}{C}}}-CH\overset{\Delta}{=}CH-CH_3$$

$$\text{CH}_3-\underset{\underset{A}{|}}{\overset{\overset{CH_3}{|}}{C}}-\underset{\underset{B}{|}}{CH}-\overset{\overset{OH}{\blacktriangledown}}{\underset{\underset{H}{|}}{\underset{\blacktriangle}{C}}}-CH\overset{\Delta'}{=}CH-CH_3$$

$$\text{CH}_3-\underset{\underset{A}{|}}{\overset{\overset{CH_3}{|}}{C}}-\underset{\underset{B}{|}}{CH}-\overset{\overset{H}{\blacktriangledown}}{\underset{\underset{O-\overset{\overset{O}{\|}}{C}-CH_3}{|}}{\underset{\blacktriangle}{C}}}-CH\overset{\Delta}{=}CH-CH_3$$

$$\text{CH}_3-\underset{\underset{A}{|}}{\overset{\overset{CH_3}{|}}{C}}-\underset{\underset{B}{|}}{CH}-\overset{\overset{O-\overset{\overset{O}{\|}}{C}-CH_3}{\blacktriangledown}}{\underset{\underset{H}{|}}{\underset{\blacktriangle}{C}}}-CH\overset{\Delta}{=}CH-CH_3$$

$$\text{CH}_3-\underset{\underset{A}{|}}{\overset{\overset{CH_3}{|}}{C}}-\underset{\underset{B}{|}}{CH}-\overset{\overset{H}{\blacktriangledown}}{\underset{\underset{O-C=CH_2\ OM}{|}}{\underset{\blacktriangle}{C}}}-CH\overset{\Delta}{=}CH-CH_3$$

$$\text{CH}_3-\underset{\underset{A}{|}}{\overset{\overset{CH_3}{|}}{C}}-\underset{\underset{B}{|}}{CH_3}-\overset{\overset{O-C=CH_2}{\blacktriangledown}\overset{OM}{|}}{\underset{\underset{H}{|}}{\underset{\blacktriangle}{C}}}-CH\overset{\Delta'}{=}CH-CH_3$$

$$\text{CH}_3-\underset{\underset{A}{|}}{\overset{\overset{CH_3}{|}}{C}}-\underset{\underset{B}{|}}{CH}-\overset{\overset{H}{\blacktriangledown}}{\underset{\underset{O-C=CH_2\ |\ R_5}{|}}{\underset{\blacktriangle}{C}}}-CH\overset{\Delta}{=}CH-CH_3$$

$$\text{CH}_3-\underset{\underset{A}{|}}{\overset{\overset{CH_3}{|}}{CH}}-\underset{\underset{B}{|}}{CH}-\overset{\overset{O-C=CH_2}{\blacktriangledown}\overset{R_5}{|}}{\underset{\underset{H}{|}}{\underset{\blacktriangle}{C}}}-CH\overset{\Delta'}{=}CH-CH_3$$

$$\text{CH}_3-\underset{\underset{A}{|}}{\overset{\overset{CH_3}{|}}{C}}-\underset{\underset{B}{|}}{CH}-CH\overset{\overset{H}{\blacktriangledown}}{\underset{\blacktriangle}{=}}CH-\underset{\underset{CH_3}{|}}{C}-CH_2-\overset{\overset{O}{\|}}{C}-R_6$$

wherein A and B and $R_6$ are as above; M is an alkali metal; $R_3$ is a radical derived from a dicarboxylic acid by removal of the hydroxy moiety of one of the carboxylic acid groups; $R_5$ is hydrogen, lower alkoxy, $$-N\begin{matrix}R_7\\ \\R_8\end{matrix} \quad \text{and} \quad -O-\underset{\underset{R_9}{|}}{\overset{\overset{R_7}{|}}{Si}}-R_8; \ R_6, R_7, R_8$$

IX-A

IX-B

X-A

X-B

X-A₁

X-B₁

XI-A

XI-B

V-A and $R_9$ are as above; Δ designates that the double bond has a cis configuration and Δ' designates that the double bond has a trans configuration.

In the first step of this invention, isovaleraldehyde or prenal, i.e., a compound of the formula:

$$\text{CH}_3-\underset{\underset{A}{|}}{\overset{\overset{CH_3}{|}}{C}}-\underset{\underset{B}{|}}{CH}-CHO$$

is converted to the compound of formula VII by reacting isovaleraldehyde or prenal with a compound of the formula:

$$CH_{3-C\,|\,C-MgX} \qquad \qquad \text{XIII}$$

wherein X is a halogen; via a Grignard reaction. Any of the conditions conventional in Grignard reactions can be utilized to carry out this conversion.

The compound of formula VII can be resolved to its optical antopodes of formula VII-A and VII-B through the reaction of the compound of formula VII with a dicarboxylic acid to form a half ester and the reaction of the half ester with an optically active base. In forming the half ester, i.e., the compound of formula VIII any conventional dicarboxylic acid can be utilized. Among the preferred dicarboxylic acids are included lower alkyl dicarboxylic acids such as oxalic acid, malonic acid, succinic acid, glutamic acid, adipic acid or aromatic carboxylic acids such as the phenyl dicarboxylic acids which include phthalic acid. The formation of the half ester is carried out by conventional means such as reacting the compound of formula VII with the dicarboxylic acid or an active derivative of the dicarboxylic acid such as the anhydride thereof. This esterification generally takes place in the presence of an organic amine base. Any conventional organic amine base such as pyridine and lower alkyl amines can be utilized. Where the organic amine base is a liquid such as pyridine, this base can be utilized as the inert solvent medium. On the other hand, any conventional inert organic solvent can be utilized in forming the half ester. In forming this half ester, temperature and pressure are not critical and this half ester can be formed at room temperature and atmospheric pressure. On the other hand, elevated or reduced temperatures and pressures can be utilized.

The half ester of formula VIII is then reacted with an optically active organic amine base such as brucine, ephedrine or quinine to produce the diastereomeric salt of the formula:

VIII-C $$\text{CH}_3-\underset{\underset{CH_3}{|}}{\overset{\overset{CH_3}{|}}{CH}}-CH_2-\underset{\underset{C\equiv C-CH_3}{|}}{CH}-\overset{\overset{O}{\|}}{C}-R_{20}-COOH\ .\ NH_2\ R_{21}$$

wherein $R_{20}$ is a divalent phenyl or lower alkyl radical and $R_{21}$ is an optically active organo radical.

Any conventional optically active organo amine base can be utilized to form the compound of formula VIII-C. Among the preferred bases are those mentioned above as well as dehydroabiethylamine, alpha-methyl benzyl amine and alpha methyl-p-nitro benzylamine. This reaction of the half ester of formula VIII with the organo amine base can be carried out in any inert organic solvent medium. Among the preferred solvents are included the ether solvents such as diethyl ether, dioxane, diglyme, tetrahydrofuran, etc. In carrying out this reaction, temperature and pressure are not critical and this reaction can be carried out at room temperature and atmospheric pressure. In this reaction, the optically active amine forms a salt with the same optical isomer of the half ester of formula VIII. This salt precipitates in solution leaving the other enantiomer of the compound of formula VIII in solution. After separating the crystallized salt from the reaction medium, the antipode of the optically active amine used previously is reacted with other enantiomer of the half ester of the compound of the formula VIII. This reaction is carried out in the same manner as with the reaction of the first enantiomer with the optically active amine. Upon reaction, the salt crystallizes from the organic solvent medium.

The respective enantiomeric salts of formula VIII-C are converted by acidification to the compounds of formula VIII-A and VIII-B after separation. Any conventional method of acidification can be utilized to cleave the separated antipodes of the compound of formula VIII-C to form the corresponding compound of formula VIII-A and VIII-B. Among the preferred methods is to treat the compound of formula VIII-C with an inorganic acid. Among the preferred inorganic acids are included sulfuric acid, phosphoric acid, hydrohalic acids such as hydrochloric, etc. This reaction is carried out at room temperature and atmospheric pressure. In carrying out this reaction, it is generally preferred to utilize an aqueous medium. Hence, this reaction is generally carried out in water. The acidification takes place in the aqueous medium at a pH of from 0.1 to 4 by the addition of acid.

The compounds of formula VIII-A and VIII-B are converted into the compounds of the formula VII-A and VII-B respectively. This conversion is generally carried out by ester hydrolysis. Any conventional method of ester hydrolysis can be utilized to carry out this conversion. A preferred method is carrying out this reaction in the presence of a base such as an alkali metal hydroxide base in an aqueous medium.

The compound of formula VII-A is converted to the compound of the formula IX-A by hydrogenation in the presence of a selective hydrogenation catalyst. Any conventional catalyst which selectively reduces only the triple bond (acetylene linkage) to a double bond can be utilized in carrying out this conversion. Among the preferred selective hydrogenation catalysts are the palladium catalysts which contain a deactivating material such as lead, lead oxide or sulfur. Among the preferred selective hydrogenation catalysts are included the palladium-lead catalysts of the type disclosed in Helvetica Chemica Acta., 35, pg. 446 (1952) and U.S. Pat. No. 2,681,938 — Lindlar. In carrying out this hydrogenation, temperature is not critical and this reaction can be carried out at room temperature. On the other hand, elevated or reduced temperatures can be utilized. Generally, this reaction is carried out in an inert organic solvent. Any conventional inert organic solvent can be utilized such as n-hexane, ethyl acetate, toluene, petroleum ether or methanol. The selective hydrogenation of a compound of the formula VII-A utilizing a selective hydrogenation catalyst produces a cis configuration across the double bond formed thereby. Therefore, the subjection of a compound of the formula VII-A to catalytic hydrogenation produces a compound of the formula IX-A where the double bond formed by the selective hydrogenation has cis configuration.

In accordance with this invention, the compound of formula VII-B is converted to the compound of formula IX-B by chemical reduction with either sodium in liquid ammonia or an aluminum hydride reducing agent. The chemical reduction of the compound of formula VII-B reduces the triple bond to a double bond which has a trans configuration. Hence, the compound of formula IX-B is formed by this chemical reduction with the double bond having a trans configuration. Where the reduction is carried out utilizing sodium in liquid ammonia, any of the conditions conventional in this type of reduction can be utilized. Generally, this reaction is carried out a temperature of from about −30° to −80° C. In this reduction, the liquid ammonia can be utilized as the reaction medium. On the other hand, a co-solvent can be present in the reaction medium along with liquid ammonia. As the co-solvents, any conventional inert organic solvent which is in liquid form at the temperature of the reaction can be utilized. Among the preferred inert organic solvents are included ether solvents such as diethyl ether, tetrahydrofuran, etc. On the other hand, the reduction can be carried out by treating the compound of formula VII-B with an aluminum hydride reducing agent. Any conventional aluminum hydride reducing agent can be utilized to carry out this reduction. Among the preferred reducing agents are the alkyl aluminum hydrides reducing agents such as diisobutyl aluminum hydride, diisoamyl aluminum hydride, etc. as well as sodium bis-[2-methoxyethoxy]-aluminum hydride. The reduction with an aluminum hydride reducing agent is carried out in an inert organic solvent medium. Any conventional inert organic solvent medium can be utilized for carrying out this reaction. Among the preferred inert organic solvents included tetrahydrofuran, pentane, dioxane, diethyl ether, hexane, toluene, benzene or xylene. Generally, temperatures of from about −120° to about 140° C. are utilized in carrying out this reduction reaction.

In accordance with this invention, when the compound of formula IX-A or IX-B is subjected to Claisen rearrangement, the compound of formula V-A is produced. In accordance with this invention, it has been found that both of the compounds of formula IX-A and IX-B undergo Claisen rearrangement to produce the compound of formula V-A. The compound of formula IX-A is converted to the compound of formula V-A via an intermediate of the formula XI-A and the compound of formula IX-B is converted to the compound of formula V-A via an intermediate of the formula XI-B. Any of the conditions conventional in Claisen rearrangement can be utilized in carrying out the conversion of either the compound formed by the compound of the formula IX-A or IX-B to a compound of the formula V-A. It is known that Claisen rearrangements occur asymetrically. See Hill, et al., *J. Org. Chem.*, Vol. 37, No. 32, 1972, pages 3737-3740, as well as Sucrow et al. *Chem. Ber.*, 104, 3689-3703 (1971), and Sucrow & Richter, *Chem. Ber.*, 104, 3679-3688 (1971). However, in the substrates utilized as starting materials in the Claisen rearrangements disclosed by Hill, asymmetric induction depends upon the presence of the optically active asymmetric carbon atom in the starting material. On the other hand, in accordance with this invention, in order to obtain by asymmetric induction through the Claisen rearrangement the desired isomer which can be converted to optically active natural vitamin E, both the proper optical configuration about the asymmetric carbon atom and the proper geometric configuration about the double bond must be present in the starting material. If the compound of the formula IX-A or IX-B is utilized in the form of a mixture of optical isomers or geometric isomers or both, one will not obtain the proper asymmetric induction through the Claisen rearrangement reaction to produce the intermediate of formula V-A which can be converted directly to optically active natural vitamin E.

The compounds of formula IX-A and IX-B are converted via the Claisen reaction to the compound of formula V-A via the intermediates in the formula of XI-A and XI-B. In carrying out this reaction, any of the conditions conventionally utilized in Claisen type rearrangement reaction such as described in the above publications can be utilized. In accordance with the preferred embodiment of this invention, the Claisen rearrangement is carried out by reacting the compounds of formula IX-A or IX-B with any one of the following reactants:

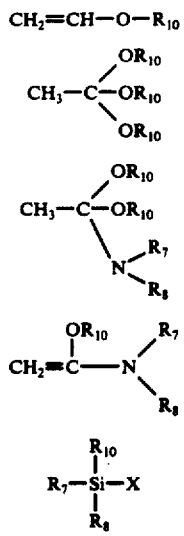

XV-A
XV-B
XV-C
XV-D
XV-E wherein $R_7$ and $R_8$ are as above, and $R_{10}$ is lower alkyl, and X is halogen The compound of formula V-A where $R_6$ is hydrogen can be formed by reacting either the compound of formula IX-A or IX-B with the vinyl ether of formula XV-A via a Claisen rearrangement reaction. Any of the conditions conventional in carrying out a Claisen rearrangement with a vinyl ether can be utilized in carrying out this reaction. Where the compound of formula IX-A is utilized, the compound of formula XI-A where $R_5$ is hydrogen is formed as an intermediate. On the other hand, where the compound of formula IX-B is utilized as the starting material, the compound of the formula XI-B where $R_5$ is hydrogen is formed as an intermediate. In converting the compound of formula IX-A and IX-B to the compound of formula XI-A and XI-B respectively, the compound of formula IX-A or IX-B is first reacted with the vinyl ether of formula XV-A. In reacting either the compound of the formula IX-A or IX-B with the compound of formula XV-A to form the compound of formula XI-A and XI-B where $R_5$ is hydrogen, temperatures of from about 40° to 150° C. are generally utilized. This reaction takes place in the presence of an acid catalyst. Any conventional acid catalyst can be utilized. Among the preferred acid catalysts are the inorganic acids such as phosphoric acid and the hydrohalic acids as well as acid salts such as mercuric acetate. On the other hand, conventional organic acid catalysts such as p-toluene sulfonic acid and p-nitrophenol can be utilized. This reaction can be carried out in an inert organic solvent. Any conventional inert organic solvent having a boiling point of greater than 40° C. can be utilized. Among the preferred solvents are the high boiling hydrocarbon solvents such as benzene, toluene, xylene, heptane, as well as ether solvents such as dimethoxyethane, diethylene glycol-dimethyl ether and dioxane. The compound of formula XI-A or XI-B where $R_5$ is hydrogen can be converted to the compound of formula V-A where $R_6$ is hydrogen by heating to a temperature of from 80° to 200° C. This reaction is carried out in the absence of any catalyst. However, the same solvent medium utilized for forming the compounds of formulas XI-A or XI-B can be utilized in carrying out this reaction.

On the other hand, the compounds of formula IX-A and IX-B can be converted to the compound of formula V-A utilizing the orthoacetate of formula XV-B. In carrying out this reaction, any of the conditions conventionally used in Claisen rearrangements with this orthoacetate can be utilized. Where the compound of formula IX-A is utilized, the compound of formula XI-A where $R_5$ is lower alkoxy forms as an intermediate. On the other hand, where the compound of formula IX-B is utilized, the compound of formula XI-B forms as an intermediate. Under the conditions of this reaction, the compound of formula XI-A and the compound of formula XI-B where $R_5$ is lower alkoxy rearranges instantaneously to produce the compound of the formula V-A where $R_6$ is lower alkoxy. In carrying out this reaction, temperatures of from 140° to 250° C. are generally utilized. This reaction is carried out in the presence of excess of the orthoacetate of formula XV-B. This is true since the orthoacetate can be utilized as the solvent medium. On the other hand, the reaction can take place in an inert organic solvent, generally those solvents having a boiling point of greater than 140° C. are preferred. Generally it is preferred to carry out this reaction in the presence of a lower alkanoic acid. If desired, the lower alkanoic acid is present in molar amounts of from about 1% to 10% per mole of the compound of formula IX-A or IX-B utilized as the starting material.

Where it is desired to produce the compound of formula V-A where

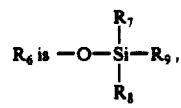

the compounds of formula IX-A and IX-B are first converted to the compounds of formula X-A and X-B respectively via acetylation with an acetic acid or reactive derivatives thereof. Any conventional method of esterifying a hydroxy group with an acetyl group can be utilized to carry out this conversion. Among the preferred methods is to react the compound of formula X-A or X-B with a reactive derivative of an acetic acid such as a halide derivative or an anhydride derivative. The compounds of formula X-A and X-B in their enolate form are then reacted with a compound of the formula XV-E to form the compound of the formula V-A via a Claisen reaction. The enolates of the compounds of formula X-A and X-B which are the compounds of formula X-A₁ and X-B₁ are produced by reacting the compounds of formula X-A and X-B respectively with an alkali metal alkyl amide base. Any conventional alkali metal alkyl amide can be utilized. The alkyl moiety can be a lower alkyl or cycloalkyl moiety which contains from 5 to 7 carbon atoms. Among the preferred bases are lithium isopropyl cyclohexyl amide and lithium diisopropyl amide. Upon reaction of the enolate of formula X-A₁ and X-B₁ with the silyl halide of formula XV-E, compounds of the formula XI-A or XI-B form, where

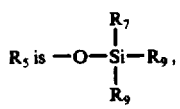

as intermediates. This reaction takes place utilizing the conditions conventional in Claisen type reactions with alkyl silyl halides. Generally, the enolates of formula X-A₁ or X-B₁ are reacted with the silyl halide in an inert organic solvent medium at a temperature of from −10° C. to −110° C. In carrying out this reaction, any conventional inert organic solvent which will not freeze at the reaction temperature can be utilized. Among the preferred solvents are tetrahydrofuran and diethyl ether.

The compounds of formula XI-A and XI-B where

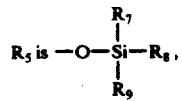

are converted to the corresponding compound of formula V-A by warming either the compound of formula XI-A or XI-B in the reaction mixture in which they were formed to a temperature of from 0° to 40° C. Therefore, in accordance with this invention, there is no need to isolate the compounds of formula XI-A and XI-B from their reaction mixture. The reaction mixture containing the compounds of formula XI-A and XI-B can be warmed to a temperature of from 0 to 40° C. to form the compound of formula V-A. On the other hand, the compound of formula XI-A and XI-B can be isolated from the reaction mixture before warming has commenced.

Where it is desired to produce the compound of formula XII where

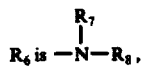

the compounds of formula IX-A and IX-B are converted to the compound of formula XI-A and XI-B where

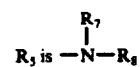

by conventional Claisen reaction utilizing conditions conventional in Claisen reactions with amides of either formulas XV-C or XV-D or mixtures thereof. In this reaction, the compounds of formula XI-B and XI-A where

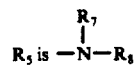

form as intermediates. This reaction is instantaneously converted under the conditions of the reaction to the compound of formula V-A. This reaction is carried out by reacting compounds of formula X-A and X-B with a compound of the formula XV-C or XV-D or mixtures thereof. This reaction is carried out at temperatures of from 120° to 250° C. in an inert organic solvent. Any conventional inert organic solvent can be utilized to carry out this reaction with high boiling solvents, i.e., solvents being above 120° C. being preferably utilized. Among the conventional inert organic solvents are included xylene and diglyme.

Where R₆ in the compound of formula V-A is other than hydrogen, the compound of formula V-A can be converted to the compound of the formula:

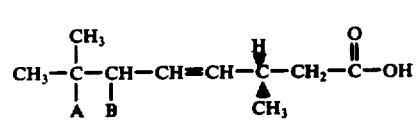

by hydrolysis by hydrolyzing the ester or amide group. Any conventional method of ester or amide hydrolysis can be utilized to affect this conversion. The silyl esters are also hydrolyzed to the compound of formula VI by conventional means. On the other hand, were R₆ in the compound of formula V-A is hydrogen, the aldehyde can be converted to the compound of the formula VI by oxidizing with a conventional oxidizing agent.

Any of the conventional oxidizing agents can be utilized. Among the preferred oxidizing agents are magnesium dioxide, silver oxide and chromic oxide. Any of the conditions conventional in utilizing these oxidizing agents can be utilized to convert the aldehyde of formula V to the compound of formula VI.

The compound of formula VI can be converted into compounds of the formula:

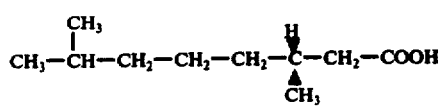

by hydrogenation utilizing a metal hydrogenation catalyst.

On the other hand, the compound of formula V-A can be converted to be saturated compound having the formula:

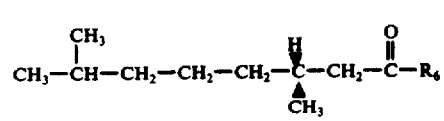

by hydrogenation, where R₆ is as above.

Any conventional hydrogenation procedure and metal hydrogenation catalyst can be utilized to carry out this procedure. Among the conventional metal hydrogenation catalysts are included palladium and platinum and Rainey nickel. After hydrogenation, the resulting compound of formula XVII is subjected to hydrolysis where $R_6$ is lower alkoxy

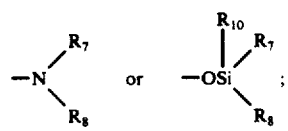

or oxidation
where $R_6$ is hydrogen. Any conventional means of ester or amide hydrolysis can be utilized to carry out this conversion. Any conventional method of oxidizing aldehydes to carboxylic acids can be utilized in this procedure for oxidizing the compound of the formula XVII where $R_6$ is hydrogen.

The compound of formula XVI and the known compound of the formula

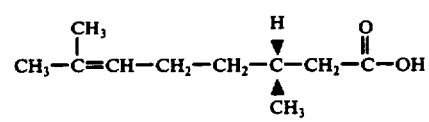

taken together as a starting material for the compound of formula III have the formula:

XVI-A

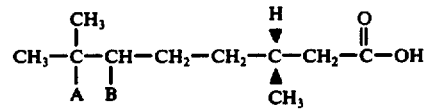

wherein A and B are as above.

The compounds of formula XVI-A can be converted into compounds of the formula III via the following intermediates:

XVIII

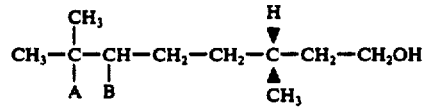

XIX

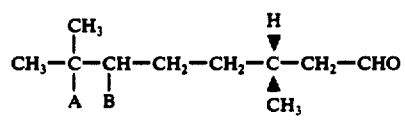

XX

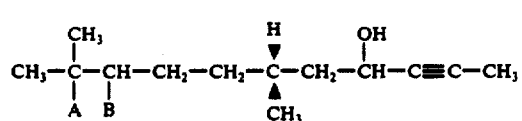

XX-A

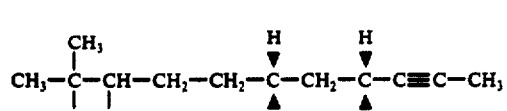

XX-B

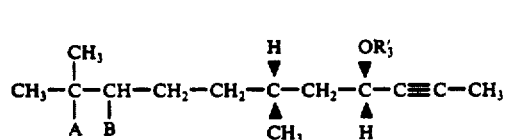

XXI-A

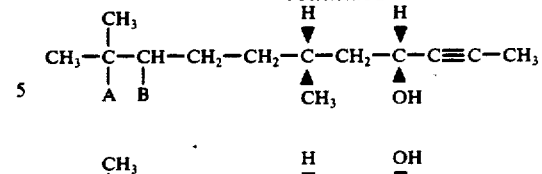

XXI-B

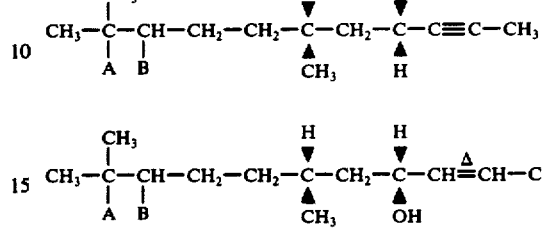

XXIII-A

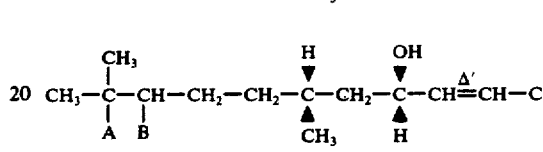

XXIII-B

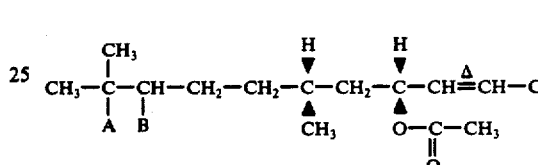

XXIV-A

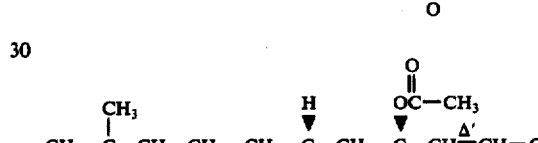

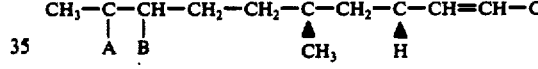

XXIV-B

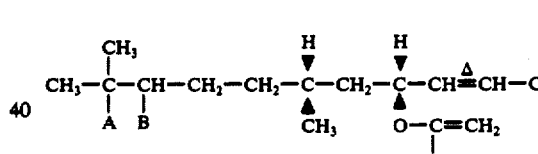

XXIV-A₁

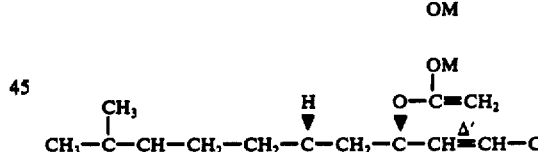

XXIV-B₁

XXV-A

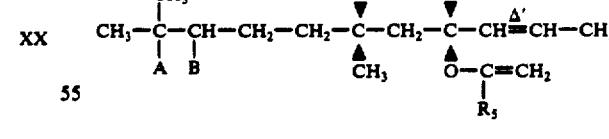

XXV-B

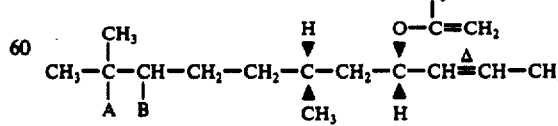

V-B

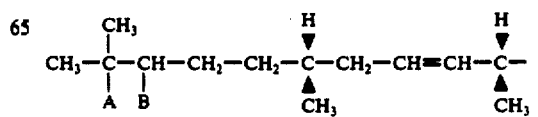

-continued

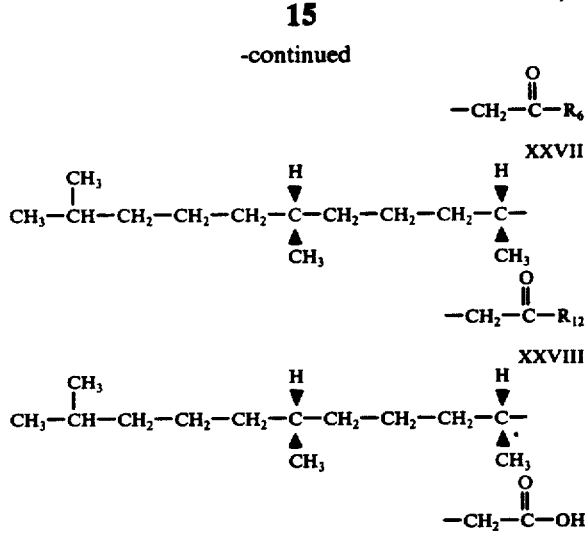

wherein A, B M, R₅, R₆ are as above; Δ designates that the double bond has a cis configuration; Δ' designates that the double bond has a trans configuration; R₁₂ is

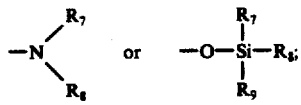

R'₃ is hydrogen or a radical derived from a monocarboxylic acid by removal of the hydroxy moiety from the acid group.

The compound of formula XVI-A can be converted into the compound of the formula XVIII by first reducing the compound of formula XVI-A to the alcohol of formula XVIII. This reduction can be carried out by utilizing an aluminum hydride reducing agent. In utilizing an aluminum hydride reducing agent, any conventional aluminum hydride reducing agent can be utilized. Among the aluminum hydride reducing agents which can be utilized are included lithium aluminum hydride, sodium aluminum hydride, diisobutyl aluminum hydride, disopropyl aluminum hydride, and sodium bis[2-methoxyethoxy]-aluminum hydride. This reduction is carried out in an inert organic solvent medium. Any conventional inert organic solvent can be utilized in carrying out this reaction. Among the preferred inert organic solvents are included tetrahydrofuran, dioxane, diethyl ether, hexane, toluene, benzene or xylene. This reaction can be carried out at room temperature, i.e., 25° C. and atmospheric pressure. On the other hand, reduced or elevated temperatures can be utilized, i.e. from −30° to about 140° C., with temperatures of from 25° to 60° C. being preferred.

The alcohol of formula XVIII can be oxidized to the aldehyde of formula XIX utilizing conventional procedures for oxidizing alcohols to aldehydes. Any of the procedures conventional in oxidizing alcohols to aldehydes can be utilized in carrying out this conversion. Among the preferred methods is utilizing an oxidizing agent such as chromic oxide, silver carbonate, chlorine in dimethylsulfoxide, dicyclohexylcarbodiimide in dimethylsulfoxide, etc. Any of the procedures conventional in oxidizing with these oxidizing agents can be utilized to convert the alcohol of formula XVIII to the aldehyde of the formula XIX. The compound of formula XIX is converted to the compound of the formula XX by a Grignard reaction with the compound of formula XIII. This reaction is carried out in the same manner as described in connection with the conversion of isovaleraldehyde to the compound of the formula VII. The compound of the formula XX as a 1:1 mixture of two diastereomers can be separated into XXI-A and XXI-B by chromatography. Any conventional method of chromatography can be utilized to achieve this separation. Among the preferred methods of separation is column chromatography or high pressure liquid chromatography. In carrying out this separation, it is generally preferred to esterify the hydroxy group in the compound of formula XX with a lower alkanoic or aroic acid. This esterification provides a clean and efficient method or separating the isomers, i.e., the compound of formulae XX-A and XX-B by chromatography. Among the preferred alkanoic or aroic acids are the phenyl or substituted phenyl carboxylic acids. Among the preferred substituted phenyl carboxylic acids are those where the phenyl group is substituted in one or more positions with a nitro, amino, lower alkyl or halo substituent. Among the preferred acids are the 3,5-dinitro benzoic acids, benzoic acid, etc. Where the compounds of the formulae XX-A and XX-B are esterified, they can be converted to the compound of formula XXI-A and XXI-B by conventional ester hydrolysis.

The compound of the formula XXI-A is converted to the compound of the formula XXIII-A via hydrogenation with a deactivated metal hydrogenation catalyst in the same manner as described in connection with the conversion of the compound of the formula VII-A to a compound of the formula IX-A. On the other hand, the compound of the formula XXI-B is converted to the compound of the formula XXIII-B by chemical reduction in the same manner as described in connection with the conversion of the compound of the formula VII-B to a compound of the formula IX-B.

The compound of the formula XXIII-A and the compound of the formula XXIII-B can be separately converted to the compound of the formula V-B by a Claisen reaction. In accordance with this invention, Claisen rearrangement preformed either on the compound of the formula XXIII-A or XXIII-B forms the specific diastereomer of the formula V-B which can be converted to optically active vitamin E. This Claisen rearrangement takes place in the same manner as described in connection with the conversion with a compound of the formula IX-A and IX-B to a compound of the formula V-A. In this reaction, the compound of the formula XXIII-A and XXIII-B are separately reacted with either a compound of the formula XV-A, XV-B, XV-C, XV-D, or XV-E with the formation of intermediates of the formula XXV-A or XXV-B. Where the compound of the formula XXIII-A is utilized, an intermediate of the formula XXV-A is formed and where the compound of the formula XXIII-B is used, an intermediate of the formula XXV-B is formed. Where the agent utilized to effect the Claisen rearrangement is a compound of the formula XV-E, the starting material is either a compound of the formula XXIV-A or XXIV-B which is converted to its enolated form, i.e., the compounds of the formula XXIV-A₁ and XXVIV-B₁ respectively. The formation of the compound of the formula XXIV-A and XXIV-B and their conversion to their enolated form, i.e., the compound of formula XXIV-A₁ or the compound of the formula XXIV-B₁ is carried out in the manner described above.

The compound of the formula V-B where R₆ is hydrogen or alkoxy can be converted to the compound of the formula III by reduction with a lithium hydride reducing agent and hydrogenation. The reduction and hydrogenation can be carried out in any desired sequence. The reduction will reduce the aldehyde or ester of formula V-B to the corresponding alcohol and the hydrogenation will reduce both double bonds formed by A and B and the double bond at the 4,5 position. If hydrogenation is carried out first, a compound of the formula:

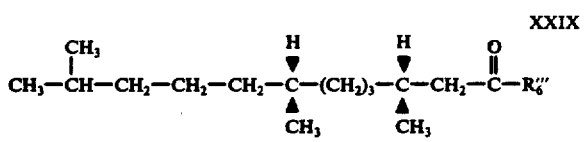
XXIX wherein R''' is hydrogen or lower alkoxy. is formed. This hydrogenation can be carried out where R''' is hydrogen or alkoxy in the same manner as described in connection with the conversion of a compound of the formula V-A to a compound of the formula XVII. The compound of the formula XXIX is converted to a compound of the formula III by reduction with an alkali metal aluminum hydride reducing agent in the manner described hereinbefore in connection with the reduction of a compound of the formula XVI-A to a compound of the formula XVIII. On the other hand, if reduction of the compound of formula V-B where R₆ is hyrogen or lower alkoxy is carried out first, a compound of the formula:

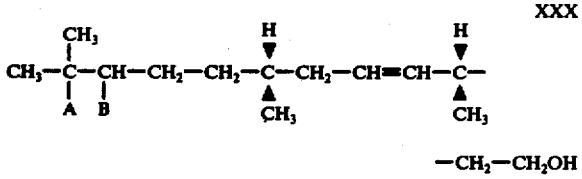
XXX wherein A and B are as above:
is formed. The compound of formula XXX is then hydrogenated to the compound of formula III. Both the hydrogenation and the reduction are carried out in the manner described hereinbefore.

Where R₆ in the compound of formula V-B forms a silyl ester or amide, this compound can be hydrolyzed by conventional methods to form the compound of the formula:

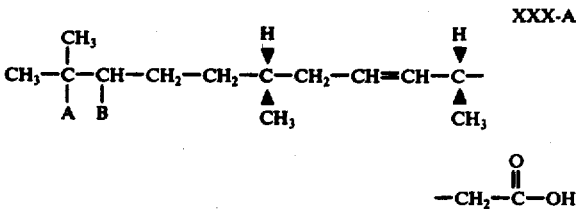
XXX-A wherein A and B are hydrogen.
Any conventional method of amide or silyl ester hydrolysis such as those described hereinbefore can be utilized to carry out this conversion. This compound can be directly converted to the compound of formula XXVIII by hydrogenation in the manner described in connection with the hydrogenation of a compound of the formula V-A.

The compound of the formula V-B where R₆ is an amide or silyl ester functional group can be converted to the compound of formula XXVII by hydrogenation in the manner described hereinbefore in connection with the hydrogenation of the compound of the formula V-A. The compound of formula XXVII can be converted to the compound of the formula XXVIII by hydrolysis. Any conventional method of amide or silyl ester hydrolysis described hereinbefore can be utilized in this conversion. The compound of the formula XXVIII is esterified by conventional means with a lower alkanol or reactive derivative thereof to form the lower alkyl ester of the compound of formula XXVIII. On the other hand, where R₆ in the compound of formula V-B is an ester, reduction of the compound of formula V-B will give the ester of the compound of formula XXIX. This ester can be converted to the compound of the formula III by reduction with an alkali metal hydride reducing agent. This reduction can be carried out in the manner described in connection with the conversion of a compound of the formula XVI-A to a compound of the formula XVIII.

The intermediates of this invention are also due to their fragrance as useful as oderants or as additives to oderant compositions. For instance, the compound of formula V-A wherein R₆ is lower alkoxy, a compound of the formula:

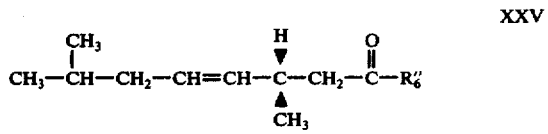
XXV wherein R₆'' is lower alkoxy;
has a fruity, woody, musty odor. On the other hand, a compound of the formula IX-B has an odor characterized as of olives, pimento, pepper and paprica. The compounds of formula XXV and IX-B are distinguished by their particular odor properties. On this basis, they can be used for perfumery purposes such as manufacture of perfumes or for perfuming products of all kinds such as cosmetic articles (soaps, powders, creams, lotions, etc). The content of compounds of formula V in odorant compositions is governed by the intended use and can vary within wide limits, for example, between 0.005–30 wt. percent.

As stated hereinabove, the novel odorant compositions produced in accordance with the present invention which have excellent odor properties, may be utilized in a wide range of odor compositions containing them. Preferable, however, they are utilized in amounts ranging from about 0.5 to about 20% by weight in the compositions comprising them. And, for example, when utilized for the perfuming soaps, between 1 and 2% by weight of such perfume compositions will suffice. In compositions such as lotions, suitably hand lotions and the like, from between 2 to about 3% by weight of such compositions are utilized and in bath salts and essences, depending on the type of composition, between 0.3 and 5% by weight of the composition are utilized.

The following examples are illustrative but not limitative of the invention. All temperatures are in degrees centigrade and the ether is diethyl ether. The term 5% pd-C designates a carbon catalyst containing 5% by weight palladium and 95% by weight carbon. The term THF designates tetrahydrofuran and the term HMDA describes hexamethylenephosphoramide. The term concentrated aqueous hydrochlorid acid designates 10 N hydrochloric acid. The term Kugelrohr designates evaporation distillation. The term Lindlar catalyst designates a catalyst prepared from palladium calcium carbonate and lead acetate as described in Organic Synthesis Collective Volume 5; pages 880–883 (1973).

EXAMPLE 1

Preparation of 6-methyl-2-heptyn-4(R,S)-ol

To a 5 l. three-necked round bottom flask equipped with a mechanical stirrer, dropping funnel and reflux condenser was added 78.5 g. (3.23 mol) of magnesium (the system was flushed with Argon) into 2 l. of dry ether. Over a period of 2½ hour was added dropwise 338 g. (3.13 mol) of ethyl bromide (freshly distilled). When the addition was completed, the reaction mixture was refluxed for 1 hour. The dropping funnel was replaced with a gas inlet tube and into the refluxing ethyl magnesium bromide solution was bubbled 143 g. (3.6 mol) of dried methyl acetylene, which was recycled six times over a period of four hours. At the end of the reaction a greenish viscous oil appeared.

The flask was cooled to 0° C. in an ice-salt bath with rapid stirring and under an Argon flow 221 g. (2.58 mol) of distilled isovaleraldehyde was added dropwise over a period of one hour at such a rate that the inside reaction temperature did not exceed 5° C. After the addition was complete, it was allowed to stir for thirty minutes. The reaction mixture was worked up by slowly pouring it into a solution of NH$_4$Cl (400 g.) in 2 l. of water with stirring. It was transferred to a separatory funnel and extracted four times with ether. The combined ether extracts were washed three times with water and dried over MgSO$_4$ and concentrated in vacuo. The crude light yellow oil was distilled at 60°/3 mmHg to yield 264 g. (81.5%) of 6-methyl-2-heptyn-4(R,S)-ol as a colorless oil.

EXAMPLE 2

Preparation (R,S)-6-methyl-2-heptyn-4-ol-hydrogenphthalate

To a 2 l. round bottom flask was added 220 g. (1.74 mol) of 6-methyl-2-heptyn-4(R,S)-ol, 265 g. (1.76 mol) of phthalic anhydride, and 220 ml. of dry pyridine. The mixture was refluxed for four hours on a steam bath. After cooling to room temperature, the content was transferred into a separatory funnel with 500 ml. of ether. The ether solution was washed with 1 N HCl (3 × 500 ml.) and extracted with 1 N NH$_4$OH (3 × 500 ml.). The combined NH$_4$OH extract was washed again with ether (2 × 500 ml.) and cooled to 0° C. It was acidified to Congo red with concentrated hydrochloric acid and extracted with CHCl$_3$ (3 × 500 ml.) The combined chloroform extract was washed with water and dried (MgSO$_4$). Evaporation of solvent to dryness at reduced pressure afforded a light brown colored residue, which was crystallized in ethanol water to give 428 g. (89.5% yield) of (R,S) -6-methyl-2-heptyn-4-ol hydrogenphthalate as white crystals, m.p. 103°–105°.

EXAMPLE 3

S- (−)-6-methyl-2-heptyn-4-ol hydrogen phthalate

To a solution of 202 g. (0.736 mol) of R,S-acid, (R,S)-6-methyl-2-heptyn-4-ol hydrogen phthalate in ether (3.0 l.) was added 122 g. (1.092 mol) of S-(−)-α-methylbenzylamine. The mixture was stirred at 25° under N$_2$ for 2.0 hours. The crystalline material was filtered off and washed again with 500 ml. of ether. It was recrystallized from methanol-ether to a constant rotation. The yield was 102.70 g of S - α - methylbenzylamine salt of S-(−)-6-methyl-2-heptyn-4-ol hydrogen-phthalate as very fine needles = m.p. 125°–136°, [α]$_D^{25}$ − 27.39° (c 1.05, CHCl$_3$).

A suspension of 102.70 g. (0.260 mol) of this salt in 100 ml. of ether and 500 ml. of 1 N HCl was stirred at 25° for 1 hour. It was washed into a separatory funnel with ether and the layers separated. The ether phase was washed with 1 N HCl and the combined aqueous phase was again extracted with ether. The combined ether extract was washed with water and dried (MgSO$_4$). Evaporation of ether to dryness at reduced pressure gave a light yellow oil, which was crystallized from ethanol-water to give 70.4 g. of S-(−)-6-methyl-2-heptyn-4-ol hydrogen phthalate as white powdered crystals, m.p. 103°–106°, [α]$_D^{25}$− 8.48° (c = 0.990, ethanol).

EXAMPLE 4

R-(+)-6-methyl-2-heptyn-4-ol hydrogen phthalate

The mother liquor from the preparation of S-α-methylbenzylamine salt of S-(−)-6-methyl-2-heptyn-4-ol hydrogen phthalate was treated with 1N HCl to give a yellow oil. Treatment of this material with 88 g. of R-(+)-α-methylbenzylamine as described in Example 3 gave 88.15 g. of R-α-methylbenzylamine salt of R-(+)-6-methyl-2-heptyn-4-ol-hydrogen phthalate as very fine needles = m.p. 128°–138° C., [α]$_D^{25}$+ 27.06° (c=1.0, CHCl$_3$).

For the preparation of R-(+)-6-methyl-2-heptyn-4-ol hydrogenphthalate, 88.15 g. of R-α-methylbenzylamine salt of R-(+)-6-methyl-2-heptyn-4-ol hydrogen phthalate was treated with 1N HCl as described in Example 3 to give after crystallization from ethanol-water 61.05 g. (30.2% yield from (R,S)-6-methyl-2-heptyn-4-ol hydrogen phthalate) of R-(+)-6-methyl-2-heptyn-4-ol hydrogen phthalate as white powdery crystals, m.p. 105°–109°, [α]$_D^{25}$= +7.81°, (c=0.986, ethanol).

EXAMPLE 5

(+)-6-methyl-2-heptyn-4(R)-ol

R-(+)-6-methyl-2-heptyn-4-ol hydrogen phthalate (119 g., 0.435 mol) in 500 ml. of 2N NaOH was refluxed with stirring for one hour. The reaction mixture was cooled to room temperature. It was then worked up by first extracting with chloroform (4 × 150 ml.). The combined chloroform extracts were washed with 1N HCl and water and dried (MgSO$_4$). Evaporation of solvent to dryness at reduced pressure gave a yellow oil, which upon distillation at 58°–59°/1.0 mmHg. afforded 44.65 g. (81.5%) of (+)-6-methyl-2-heptyn-4-(R)-ol as a colorless oil, [α]$_D^{25}$ + 13.48 (CHCl$_3$).

EXAMPLE 6

(−)-6-methyl-2-heptyn-4(S)-ol

S-(−)-6-methyl-2-heptyn-4-ol hydrogen phthalate (120 g.; 0.438 mol) in 500 ml. of 2N NaOH was refluxed with stirring for one hour. The reaction mixture was cooled to room temperature and worked up as in Example 5 to give a yellow oil, which was distilled to yield 47.12 g (86%) of (−)-6-methyl-2-heptyn-4(S)-ol as a colorless oil, b.p. 54°-55°/0.3 mmHg $[\alpha]_D^{25} - 13.02°$ ($CHCl_3$).

EXAMPLE 7

6-methyl-2-(cis)-hepten-4(R)-ol 25 g. (0.195 mol) of 6-methyl-2-heptyn-4(R)-ol was dissolved in n-hexane (300 ml.) and hydrogenated at 23° C. and 1 atmospheric pressure in the presence of 2.5 g. of palladium on calcium carbonate poisoned with lead oxide (Lindlar catalyst) and 1 ml. of quinoline. Over a period of 3¼ hours, 5.05 l. of hydrogen was absorbed. The catalyst was filtered off and washed with n-hexane. The solvent was evaporated to dryness at reduced pressure to give a colorless oil, which upon distillation at 48°-49°/1 mmHg. yielded 23.3 g. (91.7% yield) of 6-methyl-2(cis)-hepten-4(R)-ol $[\alpha]_D^{25} + 21.02°$ (c= 5.053, $CHCl_3$).

EXAMPLE 8

6-methyl-2(trans)-hepten-4(S)-ol

Into a 1 l., 3-necked round bottom flask was collected 300 ml. of dry ammonia at −78°. To this was added 11.3 g. (0.492 mol) of sodium metal in small pieces while the flask was cooled in a dry ice-acetone bath. 20 g. (0.159 mol) of 6-methyl-2-heptyn-4(S)-ol in 25 ml. of dry ether was then slowly added to the above blue solution with stirring. After addition was complete, the dry ice-acetone bath was removed, and a dry ice-acetone condenser was placed in the flask. It was refluxed for 6.0 hour (dark blue color did not fade). Ammonium chloride (2.0 g.) was slowly added until the blue color disappeared, then 50 ml. of saturated ammonium chloride solution was carefully added again. Ammonia was allowed to evaporate slowly. The solution was extracted three times with ether. The combined ether extracts were washed with three times, each with 1 N HCl and water, dried over $MgSO_4$ and concentrated in vacuo. Distillation of the crude yellow oil yielded 16.36 g. (80.5%) of 6-methyl-2(trans)-hepten-4(S)-ol as a colorless oil, b.p. 43°-44°/0.6 mmHg.

EXAMPLE 9

3(S),7-dimethyl-4(trans)-octenoic acid ethyl ester From 6-methyl-2(cis)-hepten-4(R)-ol To a 100 ml. three-necked round bottom flask equipped with distilling head and kept under Argon was added 5.0 g. (3.9 × 10⁻² mol) of 6-methyl-2(cis)-hepten-4(R)-ol, 290 mg. (3.92 × 10⁻³ mol) of propionic acid and 44.5 g. (0.274 mol) of triethyl orthoacetate. The solution was heated slowly to reflux and ethanol was distilled off. The distilling head was replaced with a reflux condenser and the solution was refluxed for 3 hours at 142° C. The excess of triethyl orthoacetate was distilled off at reduced pressure and the crude product was vacuum distilled to give 3.96 g. (51% yield) of 3(S),7-dimethyl-4(trans)-octenoic acid ethyl ester as a colorless oil, b.p. 66°-67°/0.9 mmHg., $[\alpha]_D^{25} + 19.05$ (c=4.882, $CHCl_3$).

EXAMPLE 10

3(S),7-dimethyl-4(trans)-octenoic acid

The ester, 3(S),7-dimethyl-4(trans)-octenoic acid ethyl ester (1.50 g. 7.56 × 10⁻³ mol) was refluxed in 3 ml. of 6N NaOH, 5 ml. of methanol for 2 hours. It was diluted with water (200 ml.) and extracted with diethyl ether (2 × 50 ml.). The aqueous phase was cooled in an ice-bath and acidified with concentrated hydrochloric acid to Congo red. It was then extracted with diethyl ether (3 × 50 ml.). The combined ether extracts were washed with water (2 × 50 ml.) and dried ($MgSO_4$). Evaporation of ether to dryness in a rotary evaporator gave 0.98 g. (76% yield) of 3(S),7-dimethyl-4(trans)-octenoic acid, b.p. 52°-53°/0.20 mmHg, $[\alpha]_D^{25} + 27.53$ (c=5.071, $CHCl_3$).

EXAMPLE 11

3(R),7-dimethyl octanoic acid ethyl ester

Hydrogenation: 3(S),7-dimethyl-4(trans)-octenoic acid ethyl ester (1.15 g.) was hydrogenated at 23°, atmospheric pressure in the presence of 5% Pd/C (500 mg.) in ethanol (20 ml.) for 4 hours to give 893 mg. (77% yield) of 3(R),7-dimethyl octanoic acid ethyl ester, $[\alpha]_D^{25} + 3.59°$ (c=5.268, $CHCl_3$).

EXAMPLE 12

3(R),7-dimethyl-octanoic acid

Hydrolysis: 400 mg. (2 mmol) of 3(R),7-dimethyl octanoic acid ethyl ester was refluxed in 6N NaOH (1 ml.) and methanol (4 ml.) for 2 hours. It was worked up as in Example 10 to give 207 mg. (60% yield) of 3(R),7-dimethyl octanoic acid (R-(+)-dihydrocitronellic acid), $[\alpha]_D^{25} + 6.81°$ (c=5.039, $CHCl_3$).

EXAMPLE 13

By the procedure of Example 9, 5.0 g. (3.91 × 10⁻² mol) of 6-methyl(2-trans)-hepten-4(S)-ol, 290 mg. (3.92 × 10⁻³ mol.) of propionic acid and 44.5 g. of triethylorthoacetate were reacted to produce 3.53 g. (45%) of 3(S),7-dimethyl-4(trans-octenoic acid ethyl ester as a colorless oil, b.p. 33 -35°/0.2 mmHg., $[\alpha]_D^{25} + 18.42°$ (c 5.033, $CHCl_3$).

The ester (1.01 g.) was refluxed in 2N NaOH (2 ml.) and methanol (10 ml.) for 2 hours. It was worked up as in Example 10 to give 416 mg. (48% yield) of 3(S),7-dimethyl-4(trans)-octenoic acid, b.p. 52°-55°/0.30 mmHg. $[\alpha]_D^{25} + 27.65°$ (c=5.093, $CHCl_3$).

EXAMPLE 14

Preparation of 3(R),7-dimethyl octanoic acid ethyl ester

By the procedure of Example 11, 2.43 g. of 3(S),7-dimethyl-4(trans)-octenoic acid ethyl ester obtained from example 13 was hydrogenated at 23°, atmospheric pressure in the presence of 5% Pd/C in ethanol for 2 hours. Kugelrohr distillation at 39°-45°/0.2 mmHg gave 1.796 g. of 3(R),7-dimethyl octanoic acid ethyl ester, $[\alpha]_D^{25} + 3.29°$ (c = 4.65, $CHCl_3$).

EXAMPLE 15

Preparation of 3(R),7-dimethyloctanoic acid (R-(+)-dihydrocitronellic acid)

300 mg. of 3(R),7-dimethyl octanoic acid ethyl ester obtained from example 14 was refluxed in 6N NaOH (1 ml.), methanol (4 ml.) for 2 hours. It was worked up as in Example 10 to give 226 mg. (87.5% yield) of R-(+)-dihydrocitronellic acid, b.p. 54°/0.4 mmHg. (Kugelrohr), $[\alpha]_D^{25} + 6.31°$ (c=5.069, $CHCl_3$).

EXAMPLE 16

3(S),7-dimethyl-4(trans)-octenoic acid dimethylamide

From 6-methyl-2(cis)-hepten-4(R)-ol

To a 50 ml. round bottom flask was added 2.0 g. (1.56 × 10⁻² mol) of 6-methyl-2(cis)-hepten-4(R)-ol, 4 g. of 1-dimethylamino-1,1-dimethoxyethane and 20 ml. of xylene. It was refluxed for 17 hours. The xylene was stripped off and the crude product was purified by distillation to give 2.54 g. (82.5% yield) of a pale yellow oil, b.p. 115°–166°/1.5 mmHg, $[\alpha]_D^{25}$ + 19.36° (c=5.087, CHCl$_3$).

EXAMPLE 17

Preparation of 3(R),7-dimethyl octanoic acid dimethylamide 2.0 g. of 3(S),7-dimethyl-4(trans)-octenoic acid dimethylamide in 20 ml. of methanol was hydrogenated at 22°, atmospheric pressure in the presence of 5% Pd/C (100 mg.) to give 1.89 g. of 3(R),7-dimethyl octanoic acid dimethylamide, b.p. 60°/0.4 mmHg (Kugelrohr), $[\alpha]_D^{25}$ + 1.18° (c=5.101, CHCl$_3$).

EXAMPLE 18

Preparation of 3(R),7-dimethyloctanoic acid or R-(+)-dihydrocitronellic acid

3(R),7-dimethyl octanoic acid dimethylamide (600 mg.) in 4 ml. of concentrated HCl was refluxed with stirring for 48 hours at 100°–110°. The hydrochloric acid was removed at reduced pressure. The light red brown residue was transferred to a separatory funnel with water, then with ether. The aqueous layer was extracted three times with ether. The combined ether extracts were washed with water and dried (MgSO$_4$) and concentrated in vacuo. The crude product was purified by Kugelrohr distillation at 66°/0.5 mmHg to give 431 mg. (83%) of 3(R),7-dimethyloctenoic acid or R-(+)-dihydrocitronellic acid, $[\alpha]_D^{25}$ + 6.90° (c=5.03, CHCl$_3$).

EXAMPLE 19

By the procedure of Example 16, 2.0 g. of 6-methyl-2(trans)-hepten-4(S)-ol and 4 g. of 1-dimethylamino-1,1-dimethoxy ethane were reacted in 20 ml. of xylene by refluxing for 17 hours. It was worked up as described in Example 16 to give 2.91 g. (94.5%) of 3(S),7-dimethyl-4(trans)-octenoic acid dimethylamide as a pale yellow oil, b.p. 103°–104°/0.7 mmHg. $[\alpha]_D^{25}$ + 20.64° (c=5.033, CHCl$_3$).

EXAMPLE 20

By the procedure of Example 17, 2.0 g. of 3(S),7-dimethyl-4(trans)-octenoic acid dimethylamide was hydrogenated in methanol (20 ml.) with the presence of 5% Pd-C (100 mg.) at 22°, 1 atmosphere to give 1.78 g. of 3(R),7-dimethyl octanoic acid dimethylamide as a pale yellow oil, b.p. 60°/4 mmHg (Kugelrohr).

EXAMPLE 21

Preparation of 3(R),7-dimethyloctanoic acid (R-(+)-dihydrocitronnelic acid)

The 3(R),7-dimethyl octanoic acid dimethylamide (850 mg.) was hydrolyzed in 5 ml. of concentrated aqueous HCl for 48 hours. It was worked up as in Example 18 to give 579 mg. (78.8%) of 3(R),7-dimethyloctanoic acid or R-(+)-dihydrocitronellic acid, b.p. 64°/0.4 mmHg (Kugelrohr), $[\alpha]_D^{25}$ + 6.82° (c=5.1013, CHCl$_3$).

EXAMPLE 22

6methyl-2(cis)-hepten-4(R)-ol acetate 4.0 g. of 6methyl-2(cis)-hepten-4(R)-ol in 6 ml. of acetic anhydride and 6 ml. of dry pyridine was allowed to stand at 23° C. for 17 hours. It was diluted with water and extracted three times with ether. The combined ether extracts were washed three times each with 1N HCl, water and dried (MgSO$_4$). After removal of solvent in vacuo the crude product was distilled to give 4.868 g. (91.8% yield) of 6-methyl-2(cis)-hepten-4(R)-ol acetate as a colorless oil, b.p. 39°/0.5 mmHg. $[\alpha]_D^{25}$ − 14.21° (c=4.886, CHCl$_3$).

EXAMPLE 23

6-methyl-2(trans)-hepten-4(S)-ol acetate 5.0 g. of 6-methyl-2(trans)-hepten-4(S)-ol, 7.5 ml. of acetic anhydride and 7.5 ml. of anhydrous pyridine were allowed to stand at room temperature for 17 hours. It was worked up as in Example 22 to give 6.492 g. (97.5% yield) of 6-methyl-2(trans)-hepten-4(S)-ol acetate as a colorless oil, $[\alpha]_D^{25}$ − 57.45° (c 5.0185, CHCl$_3$).

EXAMPLE 24

3(S),7-dimethyl-4(trans)-octenoic acid from 6-methyl-2(cis)-hepten-4(R)-ol acetate To a dry 100 ml. three-necked round bottom flask equipped with dropping funnel, septum and magnetic stirrer was added 4.67 ml. (10.3 mmol) of n-butyl lithium (2.2 M in n-hexane) under Argon. The flask was cooled in an ice-bath and 1.78 ml. (10.5 mmol) of N-isopropylcyclohexylamine (distilled from calcium hydride) in 2.0 ml. of anhydrous THF was added dropwise. The hexane was first removed at reduced pressure under anhydrous conditions and the flask was then cooled to −78° C. It was then charged with 3 ml. of HMPA (distilled from calcium hydride). This was followed by the slow dropwise addition of 1.702 g. (10.0 mmol) of 6-methyl-2(cis)-hepten-4(R)-ol acetate in 2 ml. of anhydrous THF. The reaction mixture was stirred for 10 minutes after addition was complete to the resulting clear yellow slurry which was formed with the lithium enolate of 6-methyl-2(cis)-hepten-4(R)-ol. To this enolate, there was then added 1.65 g. (11.0 mmol) of t-butyldimethylchlorosilane in 2 ml. of THF. The reaction mixture was stirred at −78° C. for ten minutes to allow the formation of the intermediate R[6-methyl-2(cis)-hepten-4-yl]-O-dimethyl-tertbutyl silyl ketene] and then at room temperature over a period of 2 hours. The clear light yellow solution was taken up in 300 ml. of pentane and washed with water (3 × 50 ml.), once with brine and dried (MgSO$_4$). The solvent was removed in a rotary evaporator and the crude product was distilled at 40°–50°/0.5 mmHg. to give 2.77 g. of 3(S),7-dimethyl-4(trans)-octenoic acid t-butyldimethylsilyl ester as a yellow oil.

The above silyl ester was hydrolyzed in 10% HCl (5 ml.) and THF (25 ml.) at room temperature for 17 hours. The solution was poured into 30 ml. of 5% NaOH and extracted with ether. The alkaline aqueous phase was cooled to 0° C. and acidified to Congo red with concentrated hydrochloric acid. The aqueous phase was extracted three times with ether. The ether extracts were combined, washed successively with water, saturated brine and dried (MgSO$_4$). Evaporation of ether and distillation of the crude material at 55°/0.4 mmHg. (Kugelrohr) yielded 1.06 g. (62%) of 3(S),7-dimethyl-4(trans)-octenoic acid as a colorless oil, $[\alpha]_D^{25}$ + 27.21° (c = 4.745, CHCl$_3$).

EXAMPLE 25

Preparation of 3(R),7-dimethyl-octanoic Acid 500 mg. of 3(S),7dimethyl-4(trans)-octanoic acid obtained from example 24 in ethyl acetate (20 ml.) was hydrogenated at 23° C. and atmospheric pressure in the presence of 5% Pd/C (50 mg.) for ½ hour until 70.3 ml of hydrogen was taken up. The catalyst was filtered off and washed with ethyl acetate (20 ml.). The combined filtrate was evaporated at reduced pressure to give an oil, which upon Kugelrohr distillation at 54°/0.4 mmHg gave 398 mg of pure R-(+)-dihydrocitronellic acid as a colorless oil, $[\alpha]_D^{25} + 5.93°$ (C4.652,CHCl$_3$).

EXAMPLE 26

3(S),7-dimethyl-4(trans)-octenoic acid from 6-methyl-2(trans)-hepten-4(S)-ol acetate This Example was carried out exactly the same as described in Example 24. The amount of reagents used were as follows: N-isopropyl cyclohexylamine (1.78 ml., 10.5mmol), n-butyllithium (4.67 ml.), HMPA (3 ml.), t-butyldimethylchlorosilane (1.65 g.) and 1.702 g. (10.0 mmol) of 6-methyl-2(trans)-hepten-4(S)-ol acetate. It was worked up as in Example 24 to give 2.85 g. of yellow oil containing mainly the t-butyldimethylsilylester of 3(S),7-dimethyl-4(trans)-octenoic acid. This material was treated with 10% HCl (5 ml.) in THF (25 ml.) at room temperature for 45 minutes. The solution was poured into 30 ml. of 5% aqueous NaOH and extracted with ether. The aqueous phase was cooled to 0° C. and acidified to Congo red with concentrated hydrochloric acid. It was then extracted with ether. The combined ether extracts were washed with water, saturated brine and dried. Evaporation of ether to dryness and distillation of the crude material at 56°/0.4 mmHg. (Kugelrohr) gave 873 mg. (51.2% yield) of 3(S),7-dimethyl-4(trans)-octenoic acid, $[\alpha]_D^{25} + 24.09°$ (c = 3.35, CHCl$_3$).

EXAMPLE 27

Preparation of 3(R),7-dimethyl octanoic acid or R-(+)-dihydrocitronellic acid 500 mg. of 3(S),7-dimethyl-4(trans)-octenoic acid from example 26 was hydrogenated in ethyl acetate (20 ml.), 50 mg. of 5% Pd/C at 23°. atmospheric pressure to give 488 mg. (96.5% yield) of R-(+)-dihydrocitronellic acid after distillation (Kugelrohr) at 56°/0.4 mmHg., $[\alpha]_D^{25} + 6.15°$ (c = 5.025,CHCl$_3$).

EXAMPLE 28

3(S),7-dimethyl-4-(trans)-octenal from 6-methyl-2(cis)-hepten-4(R)-ol 6-methyl-2(cis)-hepten-4(R)-ol (1.5 g., 11.7 mmol), 15 ml. of ethyl vinyl ether and 3.5 g. (11.0 mmol) of mercuric acetate were refluxed (45° C.) under Argon for 21 hours. More ethyl vinyl ether (5 ml.) and 40 ml. of benzene were added and refluxing was continued for 4 hours. The solution was cooled to room temperature and 1 ml. of glacial acetic acid was added. The reaction mixture was stirred at room temperature for one hour and then diluted with 150 ml. of ether. The solution was washed four times with 5% by weight aqueous KOH and dried over anhydrous K$_2$CO$_3$. The ether was evaporated to dryness at reduced pressure and the crude product was distilled (Kugelrohr) at 30°-60°/40 mmHg to give 1.578 g. of colorless liquid which was the vinyl ether of 6-methyl-2(cis)hepten-4(R)-ol.

The above vinyl ether was dissolved in benzene (100 ml.) and the solution was refluxed for 120 hours under Argon. The solvent was removed at reduced pressure to give a yellow oil (~ 1.289 g.). This was chromatographed on 25-g. of silica gel and elution with 1:9 parts by volume of ether:petroleum ether (b.p. 30°-60°) gave 792 mg. of material. This was further purified by Kugelrohr distillation at 36°/0.5 mmHg to yield 3(S),7-dimethyl-4trans)octenal as a colorless oil, $[\alpha]_D^{25} + 30.18°$ (c= 3.572, CHCl$_3$).

EXAMPLE 29

Conversion of 3(S),7-dimethyl-4-trans)-octenal to R -(+)-dihydrocitronellic acid To a 50 ml. round bottom flask was added 500 mg. (3.25 mole) of 3(S),7-dimethyl-4-(trans)-octenal in 10 ml. of ethanol and 1.10 g. (6.50 mmol) of silver nitrate in 20 ml. of water. To this was added dropwise 2.17 ml. (13.0 mmol) of 6 N aqueous NaOH. A black precipitate appeared and it was stirred at 23° for one ½ hours. The precipitate was filtered and washed with 15 ml. each of 0.1 N NaOh, H$_2$O and ether. The aqueous layer was separated and extracted twice with ether. It was then cooled to 0° C. and acidified to Congo red with concentrated hydrochloric acid. It was extracted with ether and the combined ether extracts were washed with warm water and dried (MgSO$_4$) and concentrated in vacuo. The crude slightly yellow material was distilled (Kugelrohr) at 56°/0.5 mmHg to give 375 mg. (68% yield) of 3(S),7-dimethyl-4(trans)-octenoic acid, $[\alpha]_D^{25} + 27.20$ (c= 5.1835, CHCl$_3$).

260 mg. of 3(S),7-dimethyl-4(trans)-octenoic acid was hydrogenated by the procedure of Example 25 at 23°, atmospheric pressure (in ethylacetate 10ml) and in the presence of 5% Pd.C (25mg) for one hr. It was worked up as in Example 25 to give after distillation (Kugelrohr 56°/0.5 mmHg.) 227 mg. (86% yield) of 3(R),7-dimetyloctanoic acid (R-(+)-dihydrocitronellic acid), $[\alpha]_D^{25} + 6.23°$ (c= 5.138 CHCl$_3$).

EXAMPLE 30

3(S),7-dimethyl-4(trans)-octenal was prepared by the procedure of Example 28 from 2.0 g. (15.6 mmol) of 6-methyl-2(trans)-hepten-4(S)-ol, 20 ml. of ethyl vinyl ether and 4.6 g. (14.4 mmol) of mercuric acetate under reflux for 21 hours. After this period, 40 ml. of benzene and 5 ml. of ethyl vinyl ether were added again and further refluxed for 4 hours. The reaction mixture was worked up as described in Example 28 and the crude material was distilled (Kugelrohr) at 35°-70°/35 mmHg to give 2.938 g. of yellow oil, which on thin layer chromatography revealed the presence of vinyl ether of 6-methyl-2(trans)-hepten-4(S)-ol and 3(S),7-dimethyl-4(trans)-octenal. This mixture of products was dissolved in 100 ml. of benzene and the solution was refluxed under Argon for 74 hours. The benzene was evaporated off at reduced pressure to give 2.52g. of crude product, which was purified by chromatography on 40g. of silica gel. Elution with 10% by volume ether in 90% volume petroleum ether (b.p. = 30°-60°) gave 1.448 g. of 3(S),7-dimethyl-4(trans)-octenal.

EXAMPLE 31

500 mg. of 3(S),7-dimethyl-4(trans)-octenal from Example 30 was treated as in Example 29 with 1.10 g. of AgNO₃ in 2 ml. of H₂O and 2.17 ml. of 6N NaOH at room temperature for 1 1/2 hour with stirring. The reaction mixture was worked up as in Example 29 and upn Kugelrohr distillation at 58°/0.06 mmHg. afforded 425 mg. of 3(S),7-dimethyl-4(trans)-octenoic acid as a colorless oil (76% yield). [α] $_D^{25}$ + 26.45° (c= 5.0145, CHCl₃).

EXAMPLE 32

335 mg. of 3(S),7-dimethyl-4(trans)-octenoic acid was hydrogenated in ethyl acetate (10 ml.) at 23°, atmospheric pressure on 5% Pd/C (30 mg). The product was purified by distillation (Kugelrohr, 56°/0.5 mmHg) to give 284 mg. of R-(+)-dihydrocitronellic acid.

EXAMPLE 33

Preparation of R-(+)-dihydrocitronellol from R-(+)-dihydrocitronellic acid

To a 25 ml. round bottom flask was added 564 mg. of R-(+)-dihydrocitronellic acid ([α] $_D^{25}$ + 6.77°, CHCl₃) in 2 ml. of absolute diethyl ether. To this solution was added 4.59 ml. of sodium bis (2-methoxyethoxy) aluminum hydride (70% by weight in benzene) in 5 ml. of diethyl ether. The solution was stirred at 25° C. for 17 hours. It was cooled in an ice-bath and 1 ml. of water was added dropwise. Then 30 ml. of water containing 1 ml. of concentrated aqueous H₂SO₄ was added again. The organic layer was separated and the aqueous phase was extracted with diethyl ether (2 × 50 ml.). The ether extracts were combined and washed with water (3 × 50 ml.), dried over anhydrous MgSO₄ and concentrated in vacuo. The crude material was distilled at 50°/0.06 mmHg (Kugelrohr oven) to give 460 mg. (88.9%) of R-(+)-dihydrocitronellol as a colorless oil, [α] $_D^{25}$ + 4.10° (c=4.003, CHCl₃).

EXAMPLE 34

Preparation of optically pure R-(+)-dihydrocitronellal [3(R),7-dimethyl-octanal]

Into a 5l three-necked flask equipped with mechanical stirrer, Deanstark trap and condenser was placed 280 g. of silver carbonate on celite (freshly prepared) 15.8 1.5 l. of toluene. 15 g. (0.10 mol) of R-(+)-dihydrocitronellol in 500 ml. of toluene was added and the reaction mixture was vigorously stirred and refluxed in an Argon atmosphere for 14 hours. It was cooled to room temperature and the black precipitate was filtered off and washed with pentane (total 1.0 l.). Evaporation of solvent to dryness in a rotary evaporator (45° C/10 mmHg) afforded a light yellow oil with strong citronellal like order. This material was quickly filtered through a short column of silica gel (150 mg.). Elution with 5% ether in petroleum ether (b.p. 30°-60°) gave 8.60 g. of aldehyde. Further elution with ether afforded R-(+)-dihydrocitronellol. The aldehyde was further purified by Kugelrohr distillation at 55°-60°/0.8 mmHg to give 7.26 g. of pure R-(+)-dihydrocitronellal as a colorless oil, [α] $_D^{25}$ + 14.07° (c=5.074, CHCl₃).

EXAMPLE 35

Preparation of 6(R),10-dimethyl-9-undecen-2-yn-4(S)-ol and 6(R)10-dimetyl-9-undecen-2-yn-4(R)-ol 150 g. (0.964 mol.) of 3(R),7-dimethyl-6-octen-1-al in 200 ml. of ether was added dropwise to a suspension of propynylmagnesium bromide (prepared from 133 g. of ethyl bromide, 32.9 g. of magnesium and 120 g. of propyne in 900 ml. of ether) at 5° with vigorous stirring. After completion, the reaction mixture was gradually warmed to room temperature and worked up in the manner of Example 1 to give 182.45g. of crude product. Distillation of this material gave 169.6 g. (90.8%) of 6(R),10-dimethyl-9-undeen-2-yn-4-(R,S)-ol as a colorless oil, b.p. 95°10.30mmHg. 22 g. of the above material was chromatographed on 2.0 kg. of silica gel. Elution with 30°-40° ether in petroleum ether gave 5.29 g. of pure 6(R),10-dimethyl-9-undecen-2-yn-4(S)-ol as the fast moving spot. [α]$_D^{25}$− 7.83° (c=2.441, CHCl₃). Further elution gave 4.0 grams of pure 6(R), 10-dimethyl-9-undecen-2-yn-4R-ol [α]$_D^{25}$ + 9.07 (c=5.038, CHCl₃).

EXAMPLE 36

6(R),10-dimethyl-2(trans)9-undecadien-4(S)-ol

Into a three-necked flask equipped with condenser, dropping funnel and magnetic stirrer was placed 2.0 g. (0.0103 mol) of 6(R),10-dimethyl-9-undecen-2-yn-4(S)-ol in 120 ml. of dry ether. The system was flushed with Argon and 3.02 ml. of sodium bis-(2-methoxyethoxy) aluminum hydride (1.0 g. atom of hydrogen per 140 cc. in benzene) in 40 ml. of dry ether was added dropwise in such a manner that a gentle reflux was maintained. After complete addition of reagent it was further refluxed for 17 hours. The reaction mixture was cooled to 0° C. and 20 ml. of dilute sulfuric acid (4:1, H₂O, H₂SO₄) was added carefully and followed by 200 ml. of water and 200 ml. of ether while stirring was continued. The layers were separated and the aqueous phase was further extracted with ether. The combined ether extract was washed with 5% NaHCO₃, brine and dried over Na₂SO₄. Evaporation of ether to dryness in vacuo afforded 1.77 g. of light yellow oil, which was purified by Kugelrohr distillation at 58°-60°/0.20 mmHg to give 1.412g. (70% yield) of 6(R),10-dimethyl-2(trans)-9-undecadien-4(S)-ol as a colorless oil.

EXAMPLE 37

6(R),10-dimethyl-2(cis)-9-undecadien-4(R)-ol 1.5 g. of 6(R),10-dimethyl-9-undecen-2-yn-4(R)-ol was dissolved in 70 ml. of n-hexane containing 0.6 ml. of quinoline was hydrogenated at 24°, atmospheric pressure, in the presence of 150 mg. of Lindlar catalyst (palladium on calcium carbonate poisoned with lead oxide). It was worked up in the manner of Example 7 to give, after distillation (Kugelrohr 48°-60°/0.07 mmHg., 1.485 g. of 6(R),10-dimethyl-1-2-(cis)-9-undecadien-4(R)-ol.

EXAMPLE 38

3(S),7(R),11-trimethyl-4(trans),10-dodecadienoic acid ethyl ester

A. From 6(R),10-dimethyl-2(trans),9-undecadien-4(S)-ol:

To a 100 ml. three-necked flask was added 1.3 g. (6.64 mmol) of 6(R),10-dimethyl-2(trans),9-undecadien-4(S)-ol, 7.54 g. (46.48 mmol) of triethyl orthoacetate and 30 mg. of propionic acid. The solution was heated to reflux slowly and ethanol was allowed to distill off. It was further refluxed for 20 hours and the excess of reagent was removed in a rotary evaporator. The crude material was distilled (Kugelrohr) at 65°/0.20 mmHg. to give 1.26g. (71.5% yield) of 3(S), 7(R), 11-trimethyl- 4(trans),10-dodecadienoic acid ethyl ester, $[\alpha]_D^{25}+$ 6.53 (c = 0.9195, n-octane).

B. From 6(R),10-dimethyl-2(cis),9-undecadien-4(R)-ol:

0.896 g. (4.57 mmol) of 6(R),10-dimethyl-2(cis),9-undecadien-4-(R)-ol, 5.2 g. (32 mmol) of triethylorthoracetate and 4 mg. of propionic acid were heated under reflux for 1 1/2 hours after all ethanol formed had been distilled off. It was worked up as in part A of this Example and the crude product (1.022 g.) was purified by chromatography on 50 g. of silica gel. The product was 3(S), 7(R),11-trimethyl-4(trans),10-dodecadienoic acid ethyl ester.

EXAMPLE 39

1.13 g. of 3(S), 7(R), 11-trimethyl-4(trans),10-dodecadienoic acid ethyl ester in ethylacetate (80 ml.) was hydrogenated at 23° C., atmospheric pressure in the presence of 5% Pd/C (113 mg.). It was worked up as in Example 11 to give 1.05 g. of 3(R), 7(R), 11-trimethyl-dodecanoic acid ethyl ester, $[\alpha]_D^{25}$ + 1.05° (c = 0.951, n-octane).

EXAMPLE 40

3(R),7(R),11-trimethyl-dodecanol-1

445 mg. of 3(R),7(R),11-trimethyl-dodecanoic acid ethyl ester and 500 mg. of lithium aluminum hydride in 40 ml. of dry ether were refluxed for 2½ hours. After this period, the excess of lithium aluminum hydride was destroyed by careful dropwise additions of 0.5 ml. of water. After the 0.5 ml. of water was added, 300 ml. 3 N aqueous sulfuric acid was added to the reaction mixture. The reaction was then extracted three times (50 cc. per time) with diethyl ether. The ether extracts were combined and washed three times with 20 cc. of 5% by weight aqueous sodium bicarbonate solution followed by three times with 30 cc. water. The ether extract was dried over anhydrous magnesium sulfate and evaporated to dryness to give 373 mg. of crude product. The product was purified by chromatography on 20 g. of silica gel and elution with 10% by volume ether in petroleum ether (b.p. = 30°–60° C.) gave 301 mg. of 3(R),7(R), 11-triemthyl-dodecanol. A sample was distilled for analysis, b.p. 95° (bath)/0.05 mmHg, $[\alpha]_D^{25}$ + 2.55° (c= 4.436, n-octane).

EXAMPLE 41

0.712 g. of 3(R), 7(R), 11-trimethyl-4(trans), 10-dodecadienoic acid ethyl ester was hydrogenated at 23° C., atmospheric pressure, in the presence of 5% Pd/C (70 mg.) in ethyl acetate. It was worked up as in Example 11 to give 496 mg. of 3(R), 7(R), 11-trimethyl-dodecanoic acid ethyl ester, $[\alpha]_D^{25}$ + 1.56° (c= 1.153, n-octane).

EXAMPLE 42

By the procedure of Example 40, 248 mg. of 3(R),7(R),11-trimethyldodecanoic acid ethyl ester was reduced with lithium aluminum hydride (270 mg.) in refluxing ether for 2 hours to yield 209 mg. of 3(R),7(R),11-trimethyl-dodecanol, $[\alpha]_D^{25}$ + 2.42° (c=0.948, n-octane).

EXAMPLE 43

PREPARATION OF 6(R),10-DIMETHYL-UNDECAN-2-YN-4(R)-OL AND 6(R),-10-DIMETHYL-UNDECAN-2-YN-4(S)-OL

Propynyl magnesium bromide was prepared as described earlier from ethyl bromide (77g, 0.405 mol, freshly distilled), magnesium (10.8 g 0.4455 mol) and methyl acetylene (approximately 100 ml at −70°) in 400 ml of absolute diethyl ether. To this well stirred mixture was added dropwise 26.4 g (0.169 mol) of 3(R), 7-dimethyloctanal (R-(+)-dihydrocitronellal) in 500 ml of dry ether while the reaction temperature was maintained between 0°–5° C with external cooling. After 45 min. all aldehyde had been added and the reaction was allowed to warm to 30° and stirred at this temperature for 1.0 hr. Thin layer chromatography analysis of the reaction mixture at this point showed the disappearance of starting material. The flask was then cooled in an ice-bath and 100 g of NH$_4$Cl in 600 ml of water was added slowly. The content was transferred to a separatory funnel and the layers separated. The aqueous phase was further extracted with ether (3 × 250 ml). The combined ether extract was filtered quickly through Celite and washed with saturated brine (3 × 500 ml) and dried over MgSO$_4$. After filtration the solvent was evaporated to dryness in a rotary evaporator (40°/25mmHg) to give 33.1 g (100%) of crude 6(R),10-dimethyl-undecan-2-yn-4(R,S)-ol as a clear light amber oil.

The crude product (33.1 g) was chromatographed on 3.36 kg of silica gel (70–230 mesh). Continued elution with a diethyl ether-petroleumether (30°–60°). Mixture containing about 10 parts by volume of diethyl ether and 90 parts by volume of petroleum-ether gave 8.53 g of 6(R), 10-dimethyl-undecan-2-yn-4(S)-ol and, 8.37 g of 6(R), 10-dimethyl-undecan-2-yn-4(R)-ol and 7.75 g mixture of the above two compounds.

EXAMPLE 44

6(R), 10-DIMETHYL-UNDECAN-2-YN-4(S)-OL 3,5-DINITROBENZOATE

First a p-toluenesulfonyl chloride (7.75 g, 40.72 mmol) in 15 ml of dry pyridine was added portionwise with stirring to a solution of 3,5-dinitrobenzoic acid (4.33 g, 20.36 mmol) in 25 ml of pyridine. The solution was chilled in ice and 4.0 g (20.36 mmol) of 6(R), 10-dimethyl-undecan-2-yn-4(S)-ol in pyridine (15 ml) was added portionwise at such a rate so that the internal temperature did not exceed 6° C. The reaction mixture was stirred at 5° for 20 min. and poured into 300 ml of ice-water. This was extracted with CHCl$_3$(4 × 200 ml). The CHCl$_3$ extract was washed with 2N HCl (3 × 200 ml), saturated aqueous NaHCO$_3$ solution (2 × 200 ml), once with brine (200 ml) and dried over anhydrous magnesium sulfate. Evaporation of chloroform to dryness in a rotary evaporator at reduced pressure gave 7.96 g of (100% yield) of crystalline crude product. This was recrystallized once from methanol to give pure 6(R), 10-dimethyl-undecan-2-yn-4(S)-ol 3,5-dinitrobenzoate, m/p. 88°–90.5° C.

EXAMPLE 45

6(R),10-DIMETHYL-UNDECAN-2-YN-4(S)-OL FROM 6(R),10-DIMETHYLUNDECAN-2-YN-4(S)-OL 3,5-DINITROBENZOATE

6(R),10-dimethyl-undecan-2-yn-4(S)-ol 3,5-dinitrobenzoate (5.4 g, 13.8 mmole) and 54 ml of 6N aqueous NaOH in 250 ml of methanol were refluxed for 1½ hr. After evaporating most methanol off in a rotary evaporator at reduced pressure, water (750 ml) was added. The aqueous phase was extracted with diethyl ether (4 × 300 ml). The combined ether extracts were washed with water (3 × 300 ml), saturated brine (300 ml) and dried (MgSO$_4$). Removal of ether at reduced pressure afforded 2.58 g (95.5% yield) of oil. This was distilled (Kugelrohr) at 87°/0.175 mmHg to give 2.10 g of pure 6(R),10-dimethyl-undecan-2-yn-4(S)-ol as a colorless oil.

EXAMPLE 46

6(R),10-DIMETHYL-UNDECAN-2-yn-4(R)-OL 3,5-DINITROBENZOATE

This compound was prepared similar to the method described in Example 44 from 4.22 g (21.6 mmol) of 6(R),10-dimethyl-undecan-2-yn-4(R)-ol,4.58 g (21.6 mmol) of 3,5-dinitrobenzoic acid and 8.25 g (43.2 mmol) of p-toluenesulfonyl chloride in dry dyridine (total 55 ml) at 4° C for 3½ hr. It was worked up as described in Example 44 to give after recrystallization once from methanol 6.73 g (84.2%) of pure 6(R),10-dimethylundecan-2-yn-4(R)-ol 3,5-dinitrobenzoate, m.p. 90°-91°.

EXAMPLE 47

6(R), 10-DIMETHYL-UNDECAN-2-YN-4(R)-OL 6.65 g (0.0171 mol) of 6(R), 10-dimethyl-undecan-2-yn-4(R)-ol 3,5-dinitrobenzoate and 35 ml of 6N aqueous NaOH is methanol (300 ml) were refluxed for 1½ hr. It was worked up as in Example 45 to give 3.30 g (98.8%) of pure 6(R),10-dimethyl-undecan-2-yn-4(R)-ol as a colorless oil.

EXAMPLE 48

6(R),10-DIMETHYL-2(TRANS)-UNDECEN-4(S)-OL

To a solution of 1.9 g (9.66 mmol) of 6(R),10-dimethylundecan-2-yn-4(S)-ol in 75 ml of dry diethyl ether was added dropwise 3.02 ml of sodium bis(2-methoxyethoxy) aluminum hydride (70% by weight in benzene, 1 g-atom Hydrogen per 140 c.c.) in 60ml of diethyl ether. The top of the condenser was fitted with an oil bubble seal and the clear solution was refluxed for 20 hr. The flask was cooled in an ice-bath and 20ml of 4:1 parts by volume H$_2$O:H$_2$SO$_4$ was added dropwise. This was followed by the addition of 200 ml of water and 200 ml of ether and the mixture was stirred for about 10 min. The aqueous phase was separated and further extracted with diethyl ether (3 × 100 ml.). The combined ether extract was washed with saturated aqueous NaHCO$_3$ solution (3 × 70 ml), water saturated brine and dried (MgSO$_4$). Evaporation of ether to dryness afforded 2.0 g of crude product, which on distillation (Kugelrohr, 85°/1.1 mmHg) gave 1.61 g (83.8% yield) of pure 6(R),10-dimethyl-2-(trans)-undecen-4(S)-ol as a colorless oil.

EXAMPLE 49

6(R),10-DIMETHYL-2-(CIS)-UNDECEN-4(R)-OL 3.2 g of 6(R),10-dimethyl-undecan-2-yn-4(R)-ol, 320 mg of Lindlar catalyst (Pd-CaCO$_3$-PbO) and quinoline (0.6 ml) in n-hexane (120 ml) were stirred and hydrogenated at 23° C, atmospheric pressure for 1.0 hr until 395 ml of hydrogen was taken up. The catalyst was filtered off and washed with 100 ml of n-hexane. The hexane was washed with 1N aqueous H$_2$SO$_4$ (3 × 30 ml), saturated aqueous NaHCO$_3$ solution (3 × 30 ml), water (3 × 30 ml) and dried (MgSO$_4$). Evaporation of solvent to dryness at reduced pressure gave 6(R),10-dimethyl-2(cis)-undecen-4(R)-ol as a colorless oil. b.p. 102°/0.2 mmHg (Kugelrohr).

EXAMPLE 50

3(S),7(R),11-TRIMETHYL-4(TRANS)-DODECENOIC ACID DIMETHYLAMIDE 850 mg of 6(R),10-dimethyl-2(cis)-undecen-4(R)-ol and 2.0 g of N,N-dimethylacetamide dimethyl acetal were refluxed in 20 ml of xylene for 20 hr. The xylene was removed at 55°/10 mmHg and the crude product was purified by Kugelrohr distillation at 68°-71°/0.15 mm to give 1.042 g (91%) of 3(S),7(R),11-trimethyl-4(trans)-dodecenoic acid dimethylamide as a light yellow oil.

EXAMPLE 51

3(R),7(R),11-TRIMETHYL DODECANOIC ACID DIMETHYLAMIDE 850 mg of 3(S),7(R),11-trimethyl-4(trans)-dodecenoic acid dimethylamide and 90 mg of 5% by weight palladium on 95% by weight charcoal were hydrogenated in 60 ml of ethylacetate for 5.0 hr. at 23° C and atmospheric pressure. The catalyst was filtered off and washed with ethylacetate. The solvent was evaporated to dryness at reduced pressure to give a crude product which was distilled at 68°-72°/0.15 mmHg (Kugelrohr) to give 750 mg of 3(R),7(R),11-trimethyl dodecanoic acid dimethylamide as a colorless oil.

EXAMPLE 52

3(S),7(R),11-TRIMETHYL-4-(TRANS)-DODECENOIC ACID ETHYL ESTER

6(R),10-dimethyl-2(cis)-undecen-4(R)-ol (2.9 g, 1.46 mmol) triethyl orthoacetate (16.5 g) and propionic acid (57 mg) were refluxed for 2.0 hr, while the ethanol formed was removed by distillation. The excess of triethyl orthoacetate was then distilled off at about 1 mmHg to give 3.904 g of residue. This was further purified by distillation (Kugelrohr) at 95°-101°/0.10 mmHg to give 3.598 g (91.1% yield) of 3(S),7(R),11-trimethyl-4-(trans)-dodecenoic acid ethyl ester as a colorless oil.

EXAMPLE 53

As described in Example 52, 1.44 g of 6(R),10-dimethyl-2-(trans)-undecen-4(S)-ol, 9.05 g of triethyl orthoacetate and 34 mg of propionic acid were refluxed for 1 hr. 45 min. under the distillation removal of ethanol. The crude product was purified by distillation (Kugelrohr, 96°-105°/0.25 mmHg) to give 1.51 g of 3(S),7(R),11-trimethyl-4(trans)-dodecenoic acid ethyl ester.

EXAMPLE 54

3(R),7(R),11-TRIMETHYL-DODECANOIC ACID ETHYL ESTER 3.53 g of 3(R),7(R),11-trimethyl-4(trans)-dodecenoic acid ethyl ester in ethyl acetate (120 ml) was hydrogenated in the presence of 360 mg of 5% by weight palladium on 95% by weight charcoal, at 23° and atmospheric pressure for 2½ hr. until no more hydrogen was absorbed (350 ml of H₂ being taken up). The catalyst was filtered off and the filtrate was evaporated to dryness at reduced pressure to give 3.55 g of colorless oil. This was purified by distillation (Kugelrohr, 101°-107°/0.15 mmHg) to yield 3.44 g of pure 3(R),7(R),11-trimethyl-dodecanoic acid ethyl ester.

EXAMPLE 55

3(R),7(R),11-TRIMETHYL-DODECANOIC ACID 145 mg of 3(R),7(R),11-trimethyl-dodecanoic acid ethyl ester and 0.5 ml of 6N aqueous NaOH were refluxed in 3 ml of methanol for 2.0 hr. The methanol was removed at reduced pressure and water (100 ml) was added. The aqueous alkaline solution was extracted with diethyl ether (2 × 30 ml), cooled in an ice-bath, and acidified with concentrated hydrochloric acid. The acidic aqueous solution was extracted with diethyl ether (3 × 20 ml). The combined ether extract was washed with water (3 × 20 ml) and dried (MgSO₄). Evaporation of ether to dryness at reduced pressure gave 107 mg of light yellow oil, which was distilled (Kugelrohr 135°-139°/0.2 mm) to yield 101 mg of 3(R),7(R),11-trimethyl-dodecanoic acid as a colorless oil.

EXAMPLE 56

3(R),7(R),10-TRIMETHYL-DODECANOL-1

3.13 g (0.01157 mol) of 3(R),7(R),10-trimethyl-dodecanoic acid ethyl ester in dry ether (35 ml) was added dropwise to a mixture of lithium aluminum hydride (3.0 g) in 150 ml of dry diethyl ether. The mixture was refluxed with stirring for 2½ hr. The flask was cooled in an ice-bath and the excess of lithium aluminum hydride was destroyed by carefully adding water, followed by 450 ml of 2N H₂SO₄. The aqueous phase was extracted with diethyl ether (3 × 150 ml). The ether extract was washed with water (3 × 50 ml), saturated aqueous NaHCO₃ (3 × 50 ml), water (3 × 50ml) and dried over anhydrous magnesium sulfate. Evaporation of ether to dryness at reduced pressure yielded 2.70 g of crude material which on distillation (Kugelrohr oven, 104°-110°/0.10 mmHg) afforded 2.572 g (97.4%) of 3(R),7(R),11-trimethyl-dodecanol as a colorless oil.

We claim:

1. A compound of the formula:

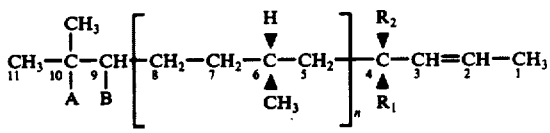

wherein A and B are individually hydrogen or, taken together, form a carbon to carbon bond; one of R₁ and R₂ is hydrogen and the other is hydroxy or lower alkanoyloxy with the proviso that when R₁ is hydroxy or lower alkanoyloxy, the 2-3 double bond has a cis configuration and when R₁ is hydrogen, the 2-3 double bond has a trans configuration and n is an integer of from 0 to 1.

2. The compound of claim 1 wherein said compounds is 6-methyl-2-(cis)-hepten-4(R)-ol.

3. The compound of claim 1 wherein said compound is 6-methyl-2-(trans)-hepten-4(S)-ol.

4. The compound of claim 1 wherein said compound is 6-methyl-2(cis)-hepten-4(R)-ol acetate.

5. The compound of claim 1 wherein said compound is 6(R),10-dimethyl-2(trans),9-undecadien-4(S)-ol.

6. The compound of claim 1 wherein said compound is 6(R),10-dimethyl-2(cis),9-undecadien-4(R)-ol.

* * * * *